United States Patent [19]

Constansa et al.

[11] Patent Number: 4,791,114

[45] Date of Patent: Dec. 13, 1988

[54] 2-BENZIMIDAZOLYLALKYLTHIO (OR -SULFINYL OR -SULFONYL) DERIVATIVES, THEIR PREPARATION AND THEIR APPLICATION AS MEDICINAL PRODUCTS

[75] Inventors: Jordi F. Constansa; Augusto C. Pinol; Juan P. Corominas, all of Barcelone, Spain

[73] Assignee: 501 Laboratorios Del, Dr. Esteve, Barcelone, Spain

[21] Appl. No.: 3,442

[22] Filed: Jan. 15, 1987

[30] Foreign Application Priority Data

Jan. 20, 1986 [FR] France ................ 86 00695

[51] Int. Cl.$^4$ ................ A61K 31/415; C07D 401/12; C07D 403/12

[52] U.S. Cl. ................ 514/256; 514/338; 544/300; 544/310; 544/316; 546/271

[58] Field of Search ........ 544/316, 310, 300; 546/271; 514/256, 338

[56] References Cited

U.S. PATENT DOCUMENTS 4,045,564 9/1977 Berntsson et al. ........ 546/271
4,619,944 10/1986 Youssefyeh et al. ........ 546/271

FOREIGN PATENT DOCUMENTS 1234058 10/1968 United Kingdom ........ 546/271

OTHER PUBLICATIONS

March, Advanced Org. Chem. pp. 363–365, 474–476.
European Jr. of Medicinal Chemistry, Beattie, L. E. et al., 18:277–285 (1983).

*Primary Examiner*—Mary C. Lee
*Assistant Examiner*—J. Richter
*Attorney, Agent, or Firm*—Fulbright & Jaworski

[57] ABSTRACT

The present invention relates to new benzimidazole derivatives, to the process for preparing them and also to their application as medicinal products.

The 2-alkylbenzimidazole derivatives according to the present invention correspond to the general formula I

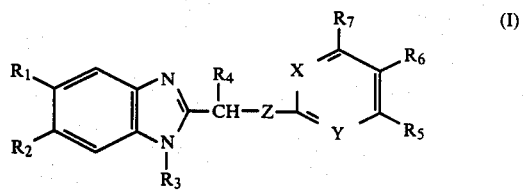

and also their therapeutically acceptable salts, in which the substituents are as defined in the specification.

6 Claims, No Drawings

2-BENZIMIDAZOLYLALKYLTHIO (OR -SULFINYL OR -SULFONYL) DERIVATIVES, THEIR PREPARATION AND THEIR APPLICATION AS MEDICINAL PRODUCTS

The present invention relates to new benzimidazole derivatives, to the process for preparing them and also to their application as medicinal products.

The compounds which are the subject of the present invention can also be used in the pharmaceutical industry as intermediates and for preparing medicinal products.

The inhibitory effects on gastric acid secretion are well documented (see in particular DE-A-No. 3,404,610; U.S. Pat. No. 4,472,409; EP-A-No. 0,074,341; EP-A-No. 0,045,200; EP-A-No. 0,005,129) for the 2-benzimidazolylthio(or -sulfinyl)alkylpyridine derivatives of general formula

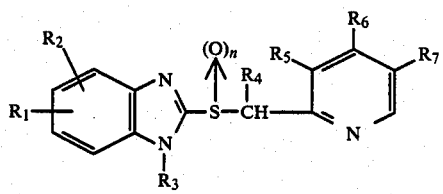

in which n denotes 0 or 1.

The new 2-benzimidazolylalkylthio(or -sulfinyl or -sulfonyl)pyridine(or -pyrimidine) derivatives which are the subject of the present invention correspond to the general formula I:

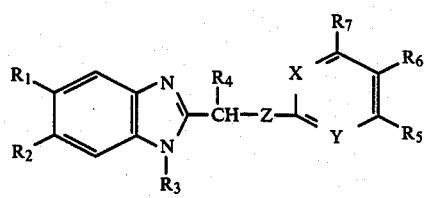

in which:
X denotes a nitrogen atom (N), or a carbon atom linked to another radical $R_8$ (C-$R_8$);
Y denotes a nitrogen atom (N) or an N-oxide group (N→O);
Z denotes a sulfur atoms (S), a sulfinyl group (S→O) or a sulfonyl group (O←S→O);
$R_1$ and $R_2$ which may be identical or different, denote a hydrogen atom, a halogen, a linear or branched $C_1$ to $C_4$ lower alkyl radical, a nitro group ($NO_2$), a trifluoromethyl group ($CF_3$), a $C_1$ to $C_4$ alkoxy or alkylthio radical, a carboxyl radical (COOH), a carboxyalkyl radical such as carboxymethyl or carboxyethyl or an alkanoyl or aryloyl radical $$(-\underset{\underset{O}{\|}}{C}-R_9);$$

$R_3$ denotes a hydrogen atom, a $C_1$ to $C_4$ lower alkyl radical or a carbonyl radical linked to another radical $R_{10}$

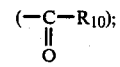

$R_4$ denotes a hydrogen atom or a $C_1$ to $C_4$ lower alkyl radical;
$R_5$ denotes a hydrogen atom, a methyl radical, a hydroxy radical or an alkoxy radical;
$R_6$ denotes a hydrogen atom, a methyl radical, a nitro radical ($NO_2$) or an alkoxy radical;
$R_7$ denotes a hydrogen atom, a $C_1$ to $C_4$ lower alkyl radical or a $C_1$ to $C_4$ alkoxy radical;
$R_8$ denotes a hydrogen atom or a methyl radical;
$R_9$ denotes a $C_1$ to $C_4$ lower alkyl radical, a $C_3$ to $C_6$ cycloalkyl radical or an aryl radical such as phenyl, and
$R_{10}$ denotes a $C_1$ to $C_4$ lower alkyl radical or an alkoxy or aryloxy or arylalkoxy radical, with the exception, however, of the compound of formula I in which:
X denotes CH,
Y denotes N,
Z denotes S, and
$R_1$ to $R_7$ denote H.

The present invention also relates to the physiologically acceptable salts of the compounds of general formula I.

The derivatives of general formula I and their salts are suitable for preventing or treating gastrointestinal diseases in mammals, including man, principally gastric acid secretion and the cytoprotective capacity.

The derivatives of general formula I can also be used in the pharmaceutical industry as intermediates and for preparing medicinal products.

The new derivatives of general formula I can be prepared according to the invention by the following methods:

METHOD A

By reaction of a compound of general formula II:

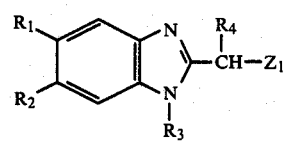

with a compound of general formula III

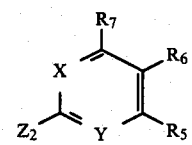

in which formulae X, Y and $R_1$ to $R_7$ have the meanings stated above, and one of the two radicals $Z_1$ and $Z_2$ consists of an -SH radical and the other is a leaving group chosen, in particular, from halogens, preferably fluorine, chlorine or bromine; radicals formed by esterified groups and which are reactive, in particular acetyloxy, tosyloxy or mesyloxy; or alternatively alkylthio or alkylsulfinyl groups, for example methylthio or methylsulfinyl.

The reaction of a compound of formula II with a compound of formula III is performed in the presence of a suitable solvent, for example alcohols such as methanol or ethanol; mixtures of these alcohols with water; or ethers such as, for example, tetrahydrofuran. This reaction is advantageously performed in the presence of a suitable base, either inorganic bases such as sodium hydroxide or sodium hydride, or organic bases such as tertiary amines. The reaction between these two compounds is performed between approximately $-5°$ C. and the boiling point of the reaction mixture.

In the compounds prepared of general formula I, X, Y and $R_1$ to $R_7$ have the meanings stated above and Z denotes a sulfur atom.

METHOD B

By reaction of a compound of general formula II with a compound of general formula III, in which formulae X and $R_1$ to $R_7$ have the meaning stated above, Y denotes an N-oxide group (N→O), $Z_1$ denotes -SH and $Z_2$ denotes a hydrogen atom.

The reaction between these two compounds is preferably performed in acetic anhydride at temperatures between 60° C. and the boiling point of the reaction mixture. In the compounds prepared of general formula I, X and $R_1$ to $R_7$ have the meanings stated above, Y denotes a nitrogen atom and Z denotes a sulfur atom.

METHOD C

By reaction of a compound of general formula IV:

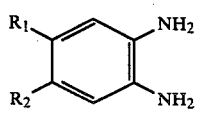
(IV)

with a compound of general formula V:

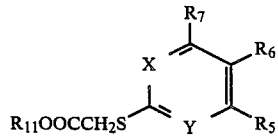
(V)

in which formulae X, Y, $R_1$, $R_2$, $R_5$, $R_6$ and $R_7$ have the meanings stated above and $R_{11}$ denotes a hydrogen atom or a lower alkyl radical such as methyl or ethyl.

The reaction of a compound of general formula IV with a compound of general formula V is preferably performed in an inorganic acid, such as hydrochloric acid or polyphosphoric acid, at temperatures between approximately 60° C. and approximately 150° C. under an atmosphere of nitrogen.

In the compounds prepared of general formula I, X, Y, $R_1$, $R_2$, $R_5$, $R_6$ and $R_7$ have the meanings stated above, $R_3$ and $R_4$ denote a hydrogen atom and Z denotes a sulfur atom.

METHOD D

By oxidation, with a stoichiometric amount of the oxidizing agent, of the compounds of general formula I in which X, Y and $R_1$ to $R_7$ have the meanings stated above and Z denotes a sulfur atom, compounds of general formula I are prepared in which X, Y and $R_1$ to $R_7$ have the meanings stated above and Z denotes a sulfinyl group (S→O).

The oxidation of the sulfur atom to a sulfinyl group is preferably performed in the presence of an oxidizing agent selected from hydrogen peroxide, peracids such as meta-chloroperbenzoic acid, nitric acid, sodium metaperiodate, chromic acid, manganese dioxide, chlorine, bromine or sulfuryl chloride. The different solvents used can be acetic acid, alcohols such as methanol or ethanol and chlorinated solvents such as methylene chloride or chloroform. The oxidation is performed at temperatures between approximately $-70°$ C. and approximately 50° C., and preferably between approximately $-20°$ C. and approximately 30° C.

Some of the new compounds can be present as optical isomers or racemates, depending on the starting substance and the process. In the case where $R_4$ denotes a substituent other than hydrogen, there are two chiral centers

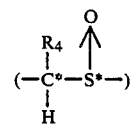

which accordingly give rise to a racemic mixture which can be separated into two diastereoisomeric pure racemates by means of chromatographic processes or by fractional crystallization. The racemates obtained can be separated to obtain their enantiomers using optically active acids so as to form salts which can be separated by differences in solubility, or recrystallization with an optically active solvent, or by means of microorganisms.

METHOD E

By oxidation of the compounds of general formula I in which X, Y and $R_1$ to $R_7$ have the meanings stated above and Z denotes a sulfur atom, with an amount two- to three-fold greter than that of the oxidizing agent, compounds of general formula I are prepared in which X, Y and $R_1$ to $R_7$ have the meanings stated above and Z denotes a sulfonyl group (O←S→O).

The oxidizing agents and the solvents are the same as those described in Method D. The oxidation reaction is performed at room temperature or at higher temperatures, up to the boiling point of the solvent.

METHOD F

By nitration, in a mixture of sulfuric and nitric acids, of the compounds of general formula I in which $R_2$ and $R_3$ denote hydrogen atoms and X, Y, Z, $R_1$, $R_4$ to $R_7$ have the meanings stated above, compounds of formula I are prepared in which X, Y, Z, $R_1$ and $R_4$ to $R_7$ have the meanings stated above, R2 denotes a nitro group ($NO_2$) and $R_3$ denotes a hydrogen atom.

The nitration reaction is performed at temperatures between $-5°$ C. and 30° C., for a time between 1 hour and 6 hours.

METHOD G

To prepare the compounds of general formula I in which $R_1$ or $R_2$ is carboxymethyl ($COOCH_3$) or carboxyethyl ($COOCH_2CH_3$), $R_3$ denotes a hydrogen atom and X, Y, Z, $R_1$ or $R_2$ and $R_4$ to $R_7$ have the meanings stated above, a compound of general formula I in which $R_1$ or $R_2$ denotes a carboxyl radical (COOH), $R_3$ denotes a hydrogen atom and $R_1$ or $R_2$, X, Y, Z and $R_4$ to $R_7$ have the meanings stated above is reacted with methanol or ethanol.

The esterification reaction is performed using the chosen alcohol as solvent and in the presence of an inorganic acid such as hydrochloric acid or an organic acid such as p-toluenesulfonic acid, at room temperature or at higher temperatures up to the boiling point of the alcohol, for a time between 2 days and two hours.

METHOD H

To prepare the compounds of general formula I in which $R_3$ denotes a $C_1$ to $C_4$ lower alkyl radical and X, Y, Z, $R_1$, $R_2$ and $R_4$ to $R_7$ have the meanings stated above, a compound of general formula I in which $R_3$ denotes a hydrogen atom and X, Y, Z, $R_1$, $R_2$ and $R_4$ to $R_7$ have the meanings stated above is reacted with an alkylating agent such as dimethyl sulfate, dimethylformamide dimethyl acetal or an alkyl halide in which the preferred halogens are chlorine, bromine and iodine.

The alkylation reaction is performed in a suitable solvent, for example the alcohols such as methanol or ethanol; ketones such as dimethylacetone; a mixture of these alcohols or ketones with water; inert solvents such as toluene; or aprotic polar solvents such as dimethylformamide. The best conditions for performing this reaction are to work in the presence of a suitable base (except when dimethylformamide dimethyl acetal is used as a reagent), either inorganic bases such as potasium hydroxide, sodium carbonate or potassium carbonate, or organic bases such as tertiary amines.

The alkylation reaction is performed at room temperature or at higher temperatures, up to the boiling point of the solvent, in a time between 2 and 24 hours.

The alkylation can also be performed under phase transfer conditions using a quaternary ammonium salt, preferably acid tetrabutylammonium sulfate, as catalyst.

In the compounds in which $R_1$ is different from $R_2$, two positional isomers are obtained in some cases, and these can be separated by fractional crystallization or by chromatographic methods.

METHOD I

To prepare the compounds of general formula I in which $R_3$ denotes a carbonyl radical linked to another radical $R_{10}$

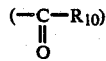

and X, Y, Z, $R_1$, $R_2$ and $R_4$ to $R_{10}$ have the meanings stated above, a compound of general formula I in which $R_3$ denotes a hydrogen atom and X, Y, Z, $R_1$, $R_2$ and $R_4$ to $R_7$ have the meanings stated above is reacted with a compound of formula VI:

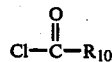    VI in which $R_{10}$ has the meaning stated above.

The reaction is performed in a suitable solvent, for example ketones such as dimethyl ketone; ethers such as tetrahydrofuran; mixtures of ketones with water; chlorinated solvents such as methylene chloride; or aprotic polar solvents such as dimethylformamide or dimethyl sulfoxide. The best conditions for carrying out this reaction are to work in the presence of a suitable base, either an inorganic base such as sodium hydride, sodium carbonate or potassium carbonate, or an organic base such as triethylamine. The most suitable temperatures fluctuate between approximately $-5°$ C. and approximately $35°$ C., the reaction time being between 1 hour and 24 hours.

For the compounds in which $R_1$ is different from $R_2$, two positional isomers as obtained in some cases, and these can be separated by fractional crystallization or by chromatographic methods.

The compounds of general formula I according to the invention can be synthesized either in the form of free base or in salt form, depending on the reaction conditions and the nature of the starting substances. The salts can be converted to free base using basic agents such as alkalis and alkali metal carbonates or by ion exchange. Moreover, the free bases synthesized can, in turn, form salts with inorganic or organic acids.

The compounds of general formula I according to the invention are preferably synthesized by Method A, and its sulfides optionally oxidized by Methods D and E; the subsequent alkylation or acylation can be performed, respectively, by Methods H or I.

The compounds of general formulae II, III, IV and V are known, or can be prepared from readily accessible compounds by processes similar to known processes. Thus, for example, the compounds of general formula II are synthesized by reaction of the compounds of general formula IV with alpha-mercaptoalkanoic acids (E. S. Milner, jun., S. Snyder and M. M. Joullié, *J. Chem. Soc.* 1964, 4151; P. Lochou, and J. Schoenieber, *Tetrahedron,* 1976, 32, 2023) or altenatively with alpha-hydroxyalkanoic acids and, in this case, subsequent optional treatment with tosyl chloride, mesyl chloride or thionyl chloride (W. R. Siegart and A. R. Day, *J. Amer. Chem. Soc.,* 1957, 79, 4391). The compounds of general formula V are synthesized by reaction of the compounds of general formula III with thioglycolic acid or an alkylthioglycolate when $Z_2$ denotes one of the leaving groups mentioned in Method A or hydrogen, and in this latter case Y denotes N→O (F. M. Hershenson and L. Bauer, *J. Org. Chem.,* 1969, 34, 655). The compounds of general formula V can also be synthesized by reaction of the compounds of general formula III, when $Z_2$ denotes SH, with an alkyl chloroacetate or an alkyl bromoacetate, in a basic medium.

In the examples which follow, the preparation of new derivatives according to the invention will be described. A few typical forms for use for the different fields of application will also be described.

The examples below, which are given simply by way of illustration, must in no way, however, limit the scope of the invention.

EXAMPLE 1

Method A

Preparation of 2-(2-benzimidazolylmethylthio)pyrimidine 10.0 g (0.06 mole) of 2-chloromethylbenzimidazole are added to a solution of 6.7 g (0.06 mole) of 2-mercaptopyrimidine and 2.4 g (0.06 mole) of sodium hydroxide in 200 ml of ethanol and 20 ml of water. The mixture is maintained under reflux for 2 hours and the ethanol evaporated off. The residue is taken up with water (50 ml) and extracted with ethyl acetate (3×50 ml), the organic phase is dried with sodium sulfate, filtered and evaporated to a volume of 40 ml of solution, in which there crystallize 10.2 g (70%) of 2-(2-benzimidazolylmethylthio)pyrimidine, melting point 154°–155° C.

The data for the identification of the product appear in Tables 1 and 2.

EXAMPLES 2 TO 18 AND 21 TO 26

The compounds identified by Examples 2 to 18 and 21 to 26 in Tables 1 and 2 are generally prepared by Methods A or C. The compounds of Examples 6, 10 and 21 to 26 can also be prepared by Method B.

EXAMPLE 6

Method B

Preparation of 5,6-dimethyl-2-(2-pyridylthiomethyl)benzimidazole

A solution of 3.84 g (0.02 mole) of 5,6-dimethyl-2-mercaptomethylbenzimidazole and 1.9 g (0.02 mole) of pyridine N-oxide in 50 ml of acetic anhydride is heated to 100° C. for 4 hours. The acetic anhydride is evaporated off, the residue taken up with acetone and the mixture filtered and concentrated to a volume of 20 ml. From this solution, 2.6 g (48%) of 5,6-dimethyl-2-(2-pyridylthiomethyl)benzimidazole crystallize. The product thereby obtained is identical to that obtained by Method A, and the data for the identification appear in Tables 1 and 2.

EXAMPLE 10

Method C

Preparation of 5-benzoyl-2-(2-pyridylthiomethyl)benzimidazole 8.45 g of 2-(2-pyridylthio)acetic acid (0.05 mole) and 10.6 g of 4-benzoyl-1,2-phenylenediamine (0.05 mole) in 100 ml of 4N hydrochloric acid are heated under reflux for 2 days. The mixture is allowed to cool and is neutralized with ammonia solution. It is extracted with ethyl acetate (3×100 ml), and the extract dried (Na$_2$SO$_4$), filtered and concentrated to a volume of 125 ml. From this solution, 11.7 g (68%) of 5-benzoyl-2-(2-pyridylthiomethyl)benzimidazole crystallize. The product thereby obtained is identical to that obtained by Method A, and the data for the identification appeat in Tables 1 and 2.

EXAMPLE 22

Method C

Preparation of 5-methoxy-2-(4-methyl-2-pyridylthiomethyl)benzimidazole 10.6 g of ethyl 2-(4-methyl-2-pyridylthio)acetate (0.05 mole) and 8.8 g of 4-methoxy-1,2-phenylenediamine hydrochloride (0.05 mole) in 400 ml of 6N hydrochloric acid are heated under reflux for 2 days. The mixture is allowed to cool and is neutralized with ammonia solution. It is extracted with ethyl acetate (3×100 ml), and the extract is dried (Na$_2$SO$_4$), filtered and concentrated to a volume of 75 ml. From this solution, 8.4 g (59%) of 5-methoxy-2-(4-methyl-2-pyridylthiomethyl)benzimidazole, melting point 138°–140° C., crystallize. The data for the identification of the product appear in Tables 1 and 2.

TABLE 1

| Example No. | X | Y | $R_1$ | $R_2$ | $R_3$ | $R_4$ | $R_5$ | $R_6$ | $R_7$ | m.p. °C. | IR (KBr) cm$^{-1}$ |
|---|---|---|---|---|---|---|---|---|---|---|---|
| 1 | N | N | H | H | H | H | H | H | H | 154–5 | 750 (Base) |
| 2 | N | N | H | H | H | H | OH | H | CH$_2$CH$_2$CH$_3$ | 234–6 | 740 (Base) |
| 3 | N | N | H | H | H | H | CH$_3$ | H | CH$_3$ | 164–7 | 750 (Base) |
| 4 | CH | N | H | H | H | H | H | NO$_2$ | H | 185–7 | 750; 1340; 1510 (Base) |
| 5 | CH | N | CH$_3$ | H | H | H | H | H | H | 133–5 | 755 (Base) |
| 6 | CH | N | CH$_3$ | CH$_3$ | H | H | H | H | H | 148–51 | 750 (Base) |
| 7 | CH | N—O | H | H | H | H | H | H | H | 193–6 | 730 (Base) |
| 8 | CH | N | Cl | H | H | H | H | H | H | 131–4 | 750 (Base) |
| 9 | CH | N | CF$_3$ | H | H | H | H | H | H | 121–7 | 765 (HCl) |
| 10 | CH | N | C$_6$H$_5$CO— | H | H | H | H | H | H | 129–34 | 760; 1665 (HCl) |
| 11 | CH | N | CH$_3$O— | H | H | H | H | H | H | 136–45 | 770 (Base) |
| 12 | CH | N | H | H | H | CH$_3$ | H | H | H | 173–5 | 750 (Base) |
| 13 | CH | N | H | H | H | H | H | H | H | 158 | 750 (Base) |
| 14 | C—CH$_3$ | N | C$_6$H$_5$CO— | H | H | H | H | CH$_3$ | H | 69–73 | 730; 1660 (Base) |
| 15 | C—CH$_3$ | N | C$_6$H$_5$CO— | H | H | H | H | H | H | 103–8 | 750; 1660 (Base) |
| 16 | C—CH$_3$ | N | H | H | H | H | H | H | H | 133–7 | 740 (Base) |
| 17 | CH | N | H | H | H | H | H | H | CH$_3$ | 147–50 | 740 (Base) |
| 18 | CH | N | CF$_3$ | H | H | H | H | H | CH$_3$ | 87–92 | 810 (Base) |
| 19 | CH | N | CH$_3$OOC— | H | H | H | H | H | CH$_3$ | 121–4 | 750; 1715 (HCl) |
| 20 | CH | N | CH$_3$OOC— | H | H | H | H | H | H | 160–2 | 750; 1710 (HCl) |
| 21 | CH | N | C$_6$H$_5$CO— | H | H | H | H | H | CH$_3$ | 165–8 | 825; 1665 (HCl) |
| 22 | CH | N | CH$_3$O | H | H | H | H | H | CH$_3$ | 138–40 | 800 (Base) |
| 23 | CH | N | CH$_3$CO— | H | H | H | H | H | CH$_3$ | 141–4 | 1695; 840 (HCl) |
| 24 | CH | N | CH$_3$ | H | H | H | H | H | CH$_3$ | 139–41 | 810 (Base) |
| 25 | CH | N | CH$_3$ | CH$_3$ | H | H | H | H | CH$_3$ | 156–9 | 805 (Base) |
| 26 | CH | N | Cl | H | H | H | H | H | CH$_3$ | 147–9 | 795 (Base) |

TABLE 2

| Example No. | $^1$H NMR $_\delta$[DMSO - d$_6$] |
|---|---|
| 1 | 8,64 (d,2H); 7,58–7,10 (m,6H); 4,72 (s,2H) |
| 2 | 7,56–7,05 (m,4H); 7,20 (br,2H); 6,01 (s,1H); 4,64 (s,2H); 2,43 (t,2H); 1,58 (Sext.,2H); 0,84 (t,3H) |
| 3 | 7,51 (m,2H); 7,14 (m,2H); 6,89 (s,1H); 6,52 (br,1H); 4,67 (s,2H); 2,34 (s,6H) |
| 4 | 9,17 (s,1H); 8,30 (m,1H); 7,65–7,00 (m,6H); 4,81 (s,2H) |
| 5 | 10,53 ,1H); 8,47 (d,1H); 7,70–6,94 (m,6H); 4,70 (s,2H); 2,39 (s,3H) |
| 6 | 8,46 (d,1H); 7,75–7,05 (m,5H); 6,05 (br,1H); 4,62 (s,2H); 2,27 (s,6H) |
| 7 | 8,45–6,90 (m,9H); 4,56 (s,2H) |
| 8 | 8,47 (d,1H); 7,70–7,00 (m,7H); 4,69 (s,2H) |
| 9 | 12,82 (br,1H); 8,47 (d,1H); 7,90–7,00 (m,6H); 4,73 (s,2H) |
| 10 | 12,75 (br,1H); 8,46 (d,1H); 7,90–7,00 (m,11H); 4,73 (s,2H) |
| 11 | 13,41 (br,1H); 8,48 (d,1H); 7,77–6,74 (m,6H); 4,64 (s,2H); 3,76 (s,3H) |
| 12 | 12,31 (br,1H); 8,50 (d,1H); 7,72–7,00 (m,7H); 5,42 (q,1H); 1,87 (d,3H) |
| 13 | 12,00 (br,1H); 8,48 (d,1H); 7,70–7,00 (m,7H); 4,73 (s,2H) |
| 14 | 9,00 (br,1H); 8,17 (s,1H); 7,87 (s,1H); 7,62 (m,7H); 7,33 (s,1H); 4,71 (s,2H); 2,28 (s,3H); 2,22 (s,3H) |
| 15 | 8,30 (d,1H); 8,00 (s,1H); 7,84–7,53 (m,9H); 7,12 (m,1H); 4,92 (s,2H); 2,26 (s,3H) |
| 16 | 8,37 (d,1H); 7,61 (br,1H); 7,52 (m,3H); 7,15 (m,3H); 4,74 (s,2H); 2,22 (s,3H) |
| 17 | 10,15 (br,1H); 8,34 (d,1H); 7,53 (m,2H); 7,21 (m,3H); 6,94 (d,1H); 4,71 (s,2H); 2,24 (s,3H) |
| 18 | 12,71 (br,1H); 8,33 (d,1H); 7,86 (s,1H); 7,69 (d,1H); 7,45 (d,1H); 7,22 (s,1H); 6,95 (d,1H); 4,71 (s,2H); 2,24 (s,3H) |
| 19 | 9,52 (br,1H); 8,32 (d,1H); 8,17 (s,1H); 7,82 (d,1H); 7,59 (d,1H); 7,19 (s,1H); 6,91 (d,1H); 4,72 (s,2H); 3,85 (s,3H); 2,21 (s,3H) |
| 20 | 12,62 (br,1H); 8,49 (d,1H); 8,14 (s,1H); 7,92–7,37 (m,4H); 7,15 (t,1H); 4,71 (s,2H); 3,87 (s,3H) |
| 21 | 10,40 (br,1H); 8,32 (d,1H); 7,97 (s,1H); 7,61 (m,7H); 7,18 (s,1H); 6,90 (d,1H); 4,75 (s,2H); 2,20 (s,3H) |

TABLE 2-continued

| Example No. | $^1$H NMR $_\delta$[DMSO - d$_6$] |
|---|---|
| 22 | 12,09 (br,1H); 8,33 (d,1H); 7,37 (d,1H); 7,23 (s,1H); 7,00 (m,2H); 6,75 (d,1H); 4,58 (s,2H); 3,76 (s,3H); 2,26 (s,3H) |
| 23 | 12,50 (br,1H); 8,31 (d,1H); 8,14 (s,1H); 7,79 (d,1H); 7,55 (d,1H); 7,19 (s,1H); 6,93 (d,1H); 4,68 (s,2H); 2,58 (s,3H); 2,23 (s,3H) |
| 24 | 11,74 (br,1H); 8,35 (d,1H); 7,39 (m,2H); 7,22 (s,1H); 6,97 (m,2H); 4,70 (s,2H); 2,41 (s,3H); 2,24 (s,3H) |
| 25 | 10,13 (br,1H); 8,33 (d,1H); 7,29 (s,2H); 7,20 (s,1H); 6,92 (s,1H); 4,66 (s,2H); 2,30 (s,6H); 2,24 (s,3H) |
| 26 | 10,70 (br,1H); 8,32 (d,1H); 7,56 (m,2H); 7,19 (m,2H); 6,92 (d,1H); 4,70 (s,2H); 2,23 (s,3H) |

EXAMPLE 27

Method D

Preparation of 5-benzoyl-2-(2-pyridylsulfinylmethyl)benzimidazole 10.1 g (0.05 mole) of 85% pure m-chloroperoxybenzoic acid are added slowly to a solution, cooled to −15° C., of 17.3 g (0.05 mole) of 5-benzoyl-2-(2-pyridylthiomethyl)benzimidazole in 250 ml of dichloromethane. The mixture is stirred at a temperature below −10° C. for 30 minutes and 100 ml of sodium carbonate solution are added. The organic phase is decanted, washed with sodium carbonate and water and then dried (Na$_2$SO$_4$). When this has been filtered, the solvent is evaporated off and the residue recrystallized in acetone. 12.0 g (66.5%) of 5-benzoyl-2-(2-pyridylsulfinylmethyl)benzimidazole, melting point 142°–145° C., are obtained.

The data for the indentification of the product appear in Tables 3 and 4.

EXAMPLES 28 TO 53

The compounds identified by Examples 28 to 53 in Tables 3 and 4 are prepared by the same method of preparation as that described in Example 27.

TABLE 3

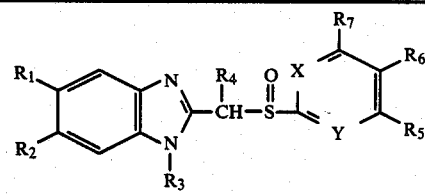

| Example No. | X | Y | R$_1$ | R$_2$ | R$_3$ | R$_4$ | R$_5$ | R$_6$ | R$_7$ | m.p. °C. | IR (KBr) cm$^{-1}$ |
|---|---|---|---|---|---|---|---|---|---|---|---|
| 27 | CH | N | C$_6$H$_5$CO— | H | H | H | H | H | H | 142-5 | 1660; 1030 (Base) |
| 28 | CH | N | H | H | H | H | H | H | H | 162-3 | 1040 (Base) |
| 29 | CH | N | H | H | H | H | H | NO$_2$ | H | 173-6 | 1530; 1360 1050 (Base) |
| 30 | CH | N | CH$_3$ | H | H | H | H | H | H | 157-9 | 1030 (Base) |
| 31 | CH | N | CH$_3$ | CH$_3$ | H | H | H | H | H | 198-9 | 1025 (Base) |
| 32 | CH | N | Cl | H | H | H | H | H | H | 176 | 1030 (Base) |
| 33 | N | N | H | H | H | H | CH$_3$ | H | CH$_3$ | 144-50 | 1050 (Base) |
| 34 | CH | N | CF$_3$ | H | H | H | H | H | H | 196-8 | 1030 (Base) |
| 35 | CH | N | CH$_3$O | H | H | H | H | H | H | 109-16 | 1035 (Base) |
| 36/37 | CH | N | H | H | H | CH$_3$ | H | H | H | 131-4 | 1040; 1050 (Base) |
| 38 | CH | N⟶O | H | H | H | H | H | H | H | 181-3 | 1045 (Base) |
| 39 | CH | N | H | H | H | H | H | H | H | 713-5 | 1035 (Hl) |

TABLE 3-continued

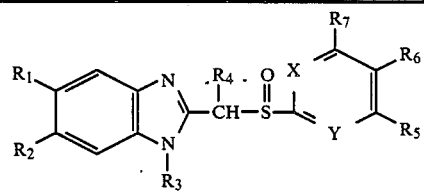

| Example No. | X | Y | R₁ | R₂ | R₃ | R₄ | R₅ | R₆ | R₇ | m.p. °C. | IR (KBr) cm⁻¹ |
|---|---|---|---|---|---|---|---|---|---|---|---|
| 40 | N | N | H | H | H | H | H | H | H | 140-5 | 1065 (Base) |
| 41 | C—CH₃ | N | C₆H₅CO— | H | H | H | H | CH₃ | H | 145-9 | 1655; 1040 (Base) |
| 42 | C—CH₃ | N | C₆H₅CO— | H | H | H | H | H | H | 156-160 | 1650; 1040 (HCl) |
| 43 | C—CH₃ | N | H | H | H | H | H | H | H | 165-8 | 1020 (Base) |
| 44 | CH | N | C₆H₅CO— | H | H | H | H | H | CH₃ | 157-161 | 1655; 1045 (HCl) |
| 45 | CH | N | CH₃OOC— | H | H | H | H | H | H | 180-1 | 1710; 1040 (Base) |
| 46 | CH | N | H | H | H | H | H | H | CH₃ | 172-6 | 1055 (HCl) |
| 47 | CH | N | CF₃ | H | H | H | H | H | CH₃ | 180-2 | 1045; 1035 (Base) |
| 48 | CH | N | CH₃OOC— | H | H | H | H | H | CH₃ | 138-40 | 1710; 1030 (Base) |
| 49 | CH | N | CH₃O | H | H | H | H | H | CH₃ | 130-5 | 1060 (HCl) |
| 50 | CH | N | CH₃CO | H | H | H | H | H | CH₃ | 148-50 | 1675; 1035 (Base) |
| 51 | CH | N | CH₃ | H | H | H | H | H | CH₃ | 169-72 | 1060 (HCl) |
| 52 | CH | N | CH₃ | CH₃ | H | H | H | H | CH₃ | 170-1 | 1020 (Base) |
| 53 | CH | N | Cl | H | H | H | H | H | CH₃ | 146-9 | 1030 (Base) |

TABLE 4

| Example No. | ¹H NMR δ[DMSO - d₆] |
|---|---|
| 27 | 12,80 (br,1H); 8,70 (d,1H); 8,13-7,40 (m,11H); 4,75 (d,1H); 4,42 (d,1H) |
| 28 | 12,50 (br,1H); 8,69 (d,1H); 8,10-7,70 (m,2H); 7,65-7,05 (m,5H); 4,77 (d,1H); 4,42 (d,1H) |
| 29 | 12,52 (br,1H); 9,50 (d,1H); 8,79 (q,1H); 7,95 (d,1H); 7,31 (m,4H); 4,79 (d,1H) 4,44 (d,1H) |
| 30 | 12,40 (br,1H); 8,69 (d,1H); 8,10-6,90 (m,6H); 4,70 (d,1H); 4,35 (d,1H); 2,38 (s,3H) |
| 31 | 12,0 (br,1H); 8,70 (q,1H); 8,02 (m,1H); 7,79 (q,1H); 7,51 (m,1H); 7,27 (s,2H) 4,64 (d,1H); 4,31 (d,1H); 2,30 (s,6H) |
| 32 | 12,65 (br,1H); 8,69 (d,1H); 8,10-7,45 (m,5H); 7,17 (q,1H); 4,70 (d,1H); 4,36 (d,1H) |
| 33 | 12,46 (br,1H); 7,53 (m,2H); 7,41 (s,1H); 7,19 (m,2H); 4,66 (d,1H); 4,49 (d,1H); 2,46 (s,6H) |
| 34 | 12,89 (br,1H); 8,72 (d,1H); 8,20-7,40 (m,6H); 4,75 (d,1H); 4,41 (d,1H) |
| 35 | 12,22 (br,1H); 8,69 (d,1H); 8,12-6,74 (m,6H); 4,67 (d,1H); 4,32 (d,1H); 3,76 (s,3H) |
| 36 | 12,30 (br,1H); 8,61 (d,1H); 7,95-7,00 (m,7H); 4,62 (q,1H); 1,74 (d,3H) |
| 37 | 12,30 (br,1H); 8,55 (d,1H); 7,90-7,28 (m,7H); 4,95 (q,1H); 1,58 (d,3H) |
| 38 | 12,41 (br,1H); 8,43 (d,1H); 7,68-7,00 (m,7H); 4,94 (d,1H); 4,69 (d,1H) |
| 39 | 11,20 (br,2H); 8,72 (d,1H); 8,10-7,83 (m,2H); 7,76-7,25 (m,5H); 4,91 (d,1H); 4,54 (d,1H) |
| 40 | 12,58 (br,1H); 8,98 (d,2H); 7,71 (d,1H); 7,58-7,10 (m,4H); 4,73 (d,1H); 4,51 (d,1H) |
| 41 | 9,47 (br,1H); 8,39 (s,1H); 7,92 (s,1H); 7,84-7,40 (m,8H); 4,78 (d,1H); 4,63 (d,1H); 2,37 (s,3H); 2,26 (s,3H) |
| 42 | 12,94 (br,1H); 8,57 (d,1H); 7,93 (s,1H); 7,67 (m,9H); 4,77 (d,1H); 4,66 (d,1H); 2,43 (s,3H) |
| 43 | 8,58 (dd,1H); 7,74 (br,1H); 7,71-7,35 (m,4H); 7,16 (m,2H); 4,73 (d,1H); 4,59 (d,1H); 2,38 (s,3H) |
| 44 | 8,54 (d,1H); 7,90 (d,1H); 7,63 (m,9H); 7,35 (d,1H); 4,73 (d,1H); 4,39 (d,1H); 2,35 (s,3H) |
| 45 | 12,81 (br,1H); 8,70 (d,1H); 8,34-7,54 (m,6H); 4,77 (d,1H); 4,44 (d,1H); 3,87 (s,3H) |
| 46 | 12,52 (br,1H); 8,54 (d,1H); 7,58 (m,3H); 7,23 (m,3H); 4,72 (d,1H); 4,37 (d,1H); 2,34 (s,3H) |
| 47 | 9,82 (br,1H); 8,53 (d,1H); 7,89 (s,1H); 7,72 (d,1H); 7,58 (s,1H); 7,47 (d,1H); 7,34 (d,1H); 4,74 (d,1H); 4,41 (d,1H); 2,33 (s,3H) |
| 48 | 12,84 (br,1H); 8,54 (d,1H); 8,16 (s,1H); 7,72 (m,3H); 7,33 (d,1H); 4,74 (d,1H); 4,41 (d,1H); 3,87 (s,3H); 2,34 (s,3H) |
| 49 | 12,24 (br,1H); 8,55 (d,1H); 7,63 (s,1H); 7,37 (m,2H); 7,03 (s,1H); 6,82 (d,1H); 4,63 (d,1H); 4,28 (d,1H); 3,78 (s,3H); 2,38 (s,3H) |
| 50 | 12,85 (br,1H); 8,54 (d,1H); 8,18 (s,1H); 7,83 (d,1H); 7,61 (s,1H); 7,56 (d,1H); 7,35 (d,1H); 4,74 (d,1H); 4,40 (d,1H); 2,62 (s,3H); 2,35 (s,3H) |
| 51 | 9,95 (br,1H); 8,56 (d,1H); 7,64 (s,1H); 7,37 (m,3H); 7,00 (d,1H); 4,64 (d,1H); 4,28 (d,1H); 2,44 (s,3H); 2,38 (s,3H) |
| 52 | 12,33 (br,1H); 8,56 (d,1H); 7,65 (s,1H); 7,36 (d,1H); 7,29 (s,2H); 4,61 (d,1H); 4,26 (d,1H); 2,40 (s,3H); 2,31 (s,6H) |
| 53 | 12,63 (br,1H); 8,50 (d,1H); 7,58 (m,2H); 7,49 (s,1H); 7,29 (d,1H); 7,16 (d,1H); 4,70 (d,1H); 4,36 (d,1H); 2,32 (s,3H) |

EXAMPLE 54

Method E

Preparation of 5-chloro-2-(2-pyridylsulfonylmethyl)benzimidazole 5.7 g (0.028 mole) of 85% pure m-chloroperoxybenzoic acid are added to a solution of 2.76 g (0.01 mole) of 5-chloro-2-(2-pyridylthiomethyl)benzimidazole in 75 ml of chloroform. The mixture is stirred at room temperature for 4 hours and 50 ml of sodium carbonate solution are added. The organic phase is decanted, washed with sodium bicarbonate and water and dried (Na₂SO₄). When this has been filtered, the solvent is evaporated off and the residue recrystallized in ethyl acetate, and 2.55 g (83%) of 5-chloro-2-(2-pyridylsulfonylmethyl)-benzimidazole, melting point 183°-186° C., are obtained.

The data for the identification of the product appear in Tables 5 and 6.

EXAMPLES 55 TO 58

The compounds identified by Examples 55 to 58 in Tables 5 and 6 are prepared by the same method of preparation as that described in Example 54.

TABLE 5

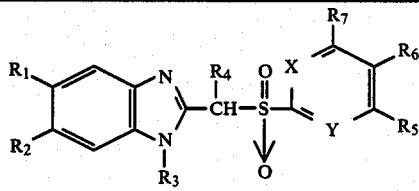

| Example No. | X | Y | $R_1$ | $R_2$ | $R_3$ | $R_4$ | $R_5$ | $R_6$ | $R_7$ | m.p. °C | IR (KBr) cm$^{-1}$ |
|---|---|---|---|---|---|---|---|---|---|---|---|
| 54 | CH | N | Cl | H | H | H | H | H | H | 183–6 | 1305; 1165 |
| 55 | CH | N | H | H | H | H | H | H | H | 213 | 1330; 1170 |
| 56 | CH | N | $CH_3$ | H | H | H | H | H | H | 171–3 | 1320; 1165; 1160 |
| 57 | CH | N | $CH_3$ | $CH_3$ | H | H | H | H | H | 212–4 | 1305; 1165 |
| 58 | CH | N | H | H | H | $CH_3$ | H | H | H | 191–5 | 1325; 1165 |

TABLE 6

| Example No. | $^1$H NMR$_\delta$[DMSO - d$_6$] |
|---|---|
| 54 | 12,30 (br,1H); 8,84 (d,1H); 8,20–7,48 (m,5H); 7,19 (d,1H); 5,14 (s,2H) |
| 55 | 12,63 (br,1H); 8,88 (d,1H); 8,25–7,70 (m,3H); 7,49 (m,2H); 7,17 (m,2H); 5,10 (s,2H) |
| 56 | 12,42 (br,1H); 8,84 (d,1H); 8,20–7,60 (m,3H); 7,35 (m,2H); 6,97 (d,1H); 5,07 (s,2H); 2,38 (s,3H) |
| 57 | 12,24 (br,1H); 8.84 (d,1H); 8,17–7,65 (m,3H); 7,25 (s,2H); 5,02 (s,2H); 2,28 (s,6H) |
| 58 | 12,37 (br,1H); 8,80 (d,1H); 8,14–7,00 (m,7H); 5,28 (q,1H); 1,75 (d,3H) |

EXAMPLE 59

Method F

Preparation of 5-nitro-2-(2-pyridylsulfinylmethyl)benzimidazole

To a solution, cooled to −5° C., of 2.57 g (0.01 mole) of 2-(2-pyridylsulfinylmethyl)benzimidazole in 20 ml of concentrated sulfuric acid, a mixture, also cooled, of 2 ml of 65% strength nitric acid and 3 ml of concentrated sulfuric acid is added in such a way that the temperature does not exceed 0° C. When the addition is complete, the mixture is maintained for one hour with stirring and poured onto ice.

The mixture is neutralized with sodium hydroxide to a pH of 7.1 to 7.2 and the product is filtered off and washed with water. When this is dry, 2.93 g (97%) of 5-nitro-2-(2-pyridylsulfinylmethyl)benzimidazole, melting point 207°–209° C., are obtained.

The data for the identification of the product appear in Tables 7 and 8.

EXAMPLE 19

Method G

Preparation of 5-carboxymethyl-2-(4-methyl-2-pyridylthiomethyl)benzimidazole A solution of 5.98 g of the acid 5-carboxy-2-(4-methyl-2-pyridylthiomethyl)benzimidazole (0.02 mole) in 100 ml of methanol saturated with hydrochloric acid is heated under reflux for 6 hours. The methanol is evaporated off and the residue taken up with 25 ml of ethanol.

From this solution, 5.82 g (93%) of 5-carboxymethyl-2-(4-methyl-2-pyridylthiomethyl)benzimidazole hydrochloride, melting point 121°–4° C., crystallize. The data for the identification of the product appear in Tables 1 and 2.

The compound identified by Example 20 in Tables 1 and 2 is prepared by the same method of preparation as that described in Example 19.

EXAMPLES 60 AND 61

Method H

Preparation of 5-benzoyl-1-methyl-2-(2-pyridylsulfinylmethyl)benzimidazole and

Preparation of 6-benzoyl-1-methyl-2-(2-pyridylsulfinylmethyl)benzimidazole

A mixture of 3.61 g of 5-benzoyl-2-(2-pyridylsulfinylmethyl)benzimidazole (0.01 mole), 0.40 g of sodium hydroxide (0.01 mole) and 2 ml of dimethyl sulfate (0.02 mole) in 50 ml of ethanol and 5 ml of water is maintained under reflux for 3 hours. The ethanol is evaporated off and the residue diluted with water and extracted with chloroform. The organic phase is washed with water, dried and evaporated. The residue is chromatographed with silica gel, using chloroform/methanol (99:1) and subsequently chloroform/methanol (95:5) as eluant. On fractional crystallization of the final fraction in ethyl acetate, 0.47 g (12.5%) of 5-benzoyl-1-methyl-2-(2-pyridylsulfinylmethyl)benzimidazole, melting point 174°–177° C., and 1.5 g (40%) of 6-benzoyl-1-methyl-2-(2-pyridylsulfinylmethyl)benzimidazole, melting point 181°–183° C., are obtained.

The data for the identification of the products corresponding to Examples 60 and 61 appear in Tables 7 and 8.

EXAMPLES 62 AND 63

Method I

Preparation of 5-benzoyl-1-carboxyethyl-2-(2-pyridylsulfinylmethyl)-benzimidazole 1.54 g of ethyl chloroformate (0.014 mole) is added to a solution of 3.61 g of 5-benzoyl-2-(2-pyridylsulfinylmethyl)benzimidazole (0.01 mole) and 1.41 g of triethylamine (0.014 mole) in 60 ml of methylene chloride. The mixture is stirred for 24 hours at room temperature and washed with dilute sodium hydroxide solution and then with water, and dried (Na$_2$SO$_4$). The organic phase is evaporated to dryness and the residue chromatographed with silica gel, using ethyl acetate as eluant, and the following two isomers are obtained: 1.2 g (27.7%) of 5-benzoyl-1-carboxyethyl-2-(2-pyridylsulfinylmethyl)benzimidazole and 1.6 g (36.9%) of 6-benzoyl-1-carboxyethyl-2-(2-pyridylsulfinylmethyl)benzimidazole.

The data for the identification of the products corresponding to Examples 62 and 63 appear in Table 7 and 8.

EXAMPLE 64

The compound identified by Example 64 in Tables 7 and 8 is prepared by the same method of preparation as that described in Examples 60 and 61.

In this test, male Wistar rats weighing 200 to 250 grams are used, the animals being maintained fasted from the day preceding that of the trail, with access to water ad libitum. A minimum of 4 animals is used in each batch.

The rats are anesthetized with ethyl ether, laporotomy is performed and the pylorus is ligated, and the abdominal incision is then sutured. The administration of the products, with the vehicle for the control batch, is performed intraduodenally (i.d.) before the abdominal incision is sutured. The dose administered for the first trail is 40 mg/kg, and the fifty percent effectove dose (ED$_{50}$) i.d. is also determined in a second trial. The vehicle used is 5% w/v gum arabic in double-distilled water.

Two hours after ligation of the pyrolus, the rats are sacrificed by prolonged anesthesia with ethyl ether, and the volume of the gastric juice is measured and the total acidity determined by means of a pH meter equipped with an automatic burette. For each product and for each dose tested, the percentage inhibition of gastric acid secretion is determined relative to the control batch.

By way of nonlimiting examples, the results obtained for a few of the derivatives of the present invention are summarized in Table 9.

TABLE 7

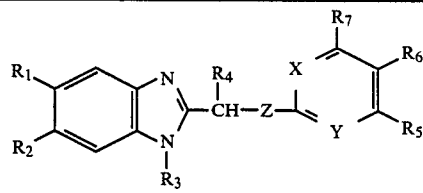

| Example No. | X | Y | Z | R$_1$ | R$_2$ | R$_3$ | R$_4$ | R$_5$ | R$_6$ | R$_7$ | Method | M.P. °C. | IR (KBr) cm$^{-1}$ |
|---|---|---|---|---|---|---|---|---|---|---|---|---|---|
| 59 | CH | N | S→O | NO$_2$ | H | H | H | H | H | H | F | 207–9 | 1515; 1345; 1040 |
| 60 | CH | N | S→O | C$_6$H$_5$CO— | H | CH$_3$ | H | H | H | H | H | 174–7 | 1660; 1050 |
| 61 | CH | N | S→O | H | C$_6$H$_5$CO— | CH$_3$ | H | H | H | H | H | 181–3 | 1650; 1046 |
| 62 | CH | N | S→O | C$_6$H$_5$CO— | H | CO$_2$CH$_2$CH$_3$ | H | H | H | H | I | | 1760; 1660; 1055 |
| 63 | CH | N | S→O | H | C$_6$H$_5$CO— | CO$_2$CH$_2$CH$_3$ | H | H | H | H | I | 142–5 | 1760; 1650; 1050 |
| 64 | CH | N | S→O | H | H | CH$_2$CH$_3$ | H | H | H | H | H | 103–5 | 1040 |

TABLE 8

| Example No. | $^1$H NMR $\delta$[DMSO - d$_6$] |
|---|---|
| 59 | 13,15 (br,1H); 8,69 (d,1H); 8,41 (s,1H); 8,04 (m,2H); 7,64 (m,3H); 4,78 (d,1H); 4,44 (d,1H) |
| 60 | 8,70 (d,1H); 8,15–7,50 (m,11H); 4,93 (d,1H); 4,62 (d,1H); 3,85 (s,3H) |
| 61 | 8,71 (d,1H); 8,10–7,50 (m,11H); 4,96 (d,1H); 4,63 (d,1H); 3,83 (s,3H) |
| 62 | 8,64 (d,1H); 8,29–7,48 (m,11H); 5,17 (d,1H); 4,71 (d,1H); 4,53 (q,2H); 1,46 (t,3H) |
| 63 | 8,64 (d,1H); 8,32–7,48 (m,11H); 5,18 (d,1H); 4,75 (d,1H); 4,47 (q,2H); 1,34 (t,3H) |
| 64 | 8,71 (d,1H); 8,15–7,16 (m,7H); 4,83 (d,1H); 4,52 (d,1H); 4,31 (q,2H); 1,34 (t,3H) |

Inhibitory activity on gastric acid secretion

Method of Shay [Shay, H.; Komarov, S. A.; Feis, S. S.; Merange, D.; Grvenstein, M.; Siplet, H.; Gastroenterology, 5, 43 (1945)—Visscher, F. E.; Seay, P. H.; Taxelaar, A. P.; Veldkamp, W.; Vander Brook, M. J.; J. Pharmac. Exp. Ther., 110, 188 (1954)—"Animal Experiments in Pharmacological Analysis", F. R. Domer; C. C. Thomas Pub., Springfield, Ill., USA, 1970, p. 140].

TABLE 9

Inhibition of gastric acid secretion in Shay rats

| Product | Percentage inhibition of gastric acid secretion (Dose = 40 mg/kg, i.d.) | ED$_{50}$ (mg/kg, i.d.) |
|---|---|---|
| Example 1 | 98 | 13 |
| Example 3 | 88 | 16 |
| Example 4 | 74 | 21 |
| Example 6 | 92 | 19 |
| Example 7 | 95 | 19 |
| Example 10 | 93 | 14 |
| Example 27 | 95 | 7 |
| Example 28 | 90 | 8 |
| Example 29 | 90 | 4 |
| Example 31 | 96 | 15 |
| Example 32 | 92 | 17 |
| Example 41 | 80 | 10 |

TABLE 9-continued
Inhibition of gastric acid secretion in Shay rats

| Product | Percentage inhibition of gastric acid secretion (Dose = 40 mg/kg, i.d.) | $ED_{50}$ (mg/kg, i.d.) |
|---|---|---|
| Example 44 | 66 | 10 |
| Example 54 | 70 | 24 |
| Example 60 | 75 | 21 |
| Example 63 | 81 | 16 |

Acute toxicity in mice

Method of Litchfield and wilcoxon [Litchfield, J. T. and Wilcoxon, E. J., H. Pharmacol. Exp. Therap., 96, 19–113 (1949)].

The product is administered orally, suspended in 5% gum arabic in double-distilled water. The volume administered is 10 ml/kg. The fifty percent lethal dose ($LD_{50}$) is calculated according to the method cited.

By way of nonlimiting examples, the results obtained for a few of the derivatives of the present invention are summarized in Table 10.

TABLE 10

| Product | Sex | Oral $LD_{50}$ (mg/kg) |
|---|---|---|
| Example 1 | ♂ | 3200 |
|  | ♀ | 2700 |
| Example 3 | ♂ | >3200 |
|  | ♀ | >3200 |
| Example 27 | ♂ | 3200 |
|  | ♀ | 3200 |
| Example 28 | ♂ | 3200 |
|  | ♀ | 3200 |
| Example 29 | ♂ | 2400 |
|  | ♀ | 2400 |
| Example 31 | ♂ | >6400 |
|  | ♀ | >6400 |

In human therapy, the dose for administration of the derivatives of the present invention naturally depends on the severity of the condition to be treated; it will be generally between approximately 30 and approximately 60 mg/day. The derivatives of the invention will be administered, for example, in the form of tablets or injectable ampoules.

By way of examples, two particular galenical forms of the derivatives which are the subject of the present invention will be described below.

EXAMPLE OF FORMULA PER TABLET

| 30-mg tablets | |
|---|---|
| Example 27 | 0.030 g |
| Lactose | 0.0342 g |
| Starch | 0.030 g |
| Polyvinylpyrrolidone | 0.006 g |
| Microcrystalline cellulose | 0.018 g |
| Colloidal silica | 0.0012 g |
| Magnesium stearate | 0.0006 g |
|  | 0.120 g |
| 60-mg tablets | |
| Example 27 | 0.060 g |
| Lactose | 0.0684 g |
| Starch | 0.060 g |
| Polyvinylpyrrolidone | 0.012 g |
| Microcrystalline cellulose | 0.036 g |
| Colloidal silica | 0.0024 g |
| Magnesium stearate | 0.0012 g |
|  | 0.240 g |

EXAMPLE OF FORMULA PER INJECTABLE AMPOULE

| Injectable ampoules, 6 mg/ml | |
|---|---|
| Example 27 | 0.030 g |
| Sodium chloride q.s. | 0.050 g |
| Ascorbic acid | 0.005 g |
| Water for injections q.s. | 5 ml |

We claim:

1. 2-Alkylbenzimidazole derivatives corresponding to the formula:

$$R_1 \text{-benzimidazole-} CH(R_4)\text{-}Z\text{-}\underset{Y}{\overset{X}{\diagdown}}\text{ring}(R_5, R_6, R_7) \quad (I)$$

and their pharmaceutically acceptable salts in which formula:

X denotes a nitrogen atom (N), or a carbon atom linked to another radical $R_8$ (C-$R_8$);

Y denotes a nitrogen atom (N) or an N-oxide group (N→O);

Z denotes a sulfur atom (S), a sulfinyl group (S→O) or a sulfonyl group (O←S→O);

$R_1$ and $R_2$, which may be identical or different, denote a hydrogen atom, a halogen, a linear or branched $C_1$ to $C_4$ lower alkyl radical, a nitro group ($NO_2$), a trifluoromethyl group ($CF_3$), a $C_1$ to $C_4$ alkoxy or alkylthio radical, a carboxyl radical (COOH), a $C_1$ to $C_4$ carboxyalkyl radical or a $C_1$ to $C_4$ alkanoyl or aryloyl radical $$(-\underset{\underset{O}{\parallel}}{C}-R_9);$$

$R_3$ denotes a hydrogen atom, a $C_1$ to $C_4$ lower alkyl radical or a carbonyl radical linked to another radical $R_{10}$ $$(-\underset{\underset{O}{\parallel}}{C}-R_{10});$$

$R_4$ denotes a hydrogen atom or a $C_1$ to $C_4$ lower alkyl radical;

$R_5$ denotes a hydrogen atom, a methyl radical, a hydroxy radical or a $C_1$ to $C_4$ alkoxy radical;

$R_6$ denotes a hydrogen atom, a methyl radical, a nitro radical ($NO_2$) or a $C_1$ to $C_4$ alkoxy radical;

$R_7$ denotes a hydrogen atom, a $C_1$ to $C_4$ lower alkyl radical or a $C_1$ to $C_4$ alkoxy radical;

$R_8$ denotes a hydrogen atom or a methyl radical;

$R_9$ denotes a $C_1$ to $C_4$ lower alkyl radical, a $C_3$ to $C_6$ cycloalkyl radical or an aryl radical, and $R_{10}$ denotes a $C_1$ to $C_4$ lower alkyl radical or a $C_1$ to $C_4$ alkoxy or aryloxy or arylalkoxy radical, wherein said aryl groups are single ring hydrocarbons; with the exception, however, of the compound of formula I in which:

X denotes CH,

Y denotes N,

Z denotes S, and
$R_1$ to $R_7$ denote H.

2. A 2-Alkylbenzimidazole derivative selected from the group consisting of:
2-(2-benzimidazolylmethylthio)pyrimidine;
2-(2-benzimidazolylmethylthio)-4-hydroxy-6-(n-propyl)pyrimidine;
2-(benzimidazolymethylthio)-4,6-dimethylpyrimidine;
2-(5-nitro-2-pyridylthiomethyl)benzimidazole;
5-methyl-2-(2-pyridylthiomethyl)benzimidazole;
5,6-dimethyl-2-(2-pyridylthiomethyl)benzimidazole;
2-(1-oxido-2-pyridylthiomethyl)benzimidazole;
5-chloro-2-(2-pyridylthiomethyl)benzimidazole;
5-trifluoromethyl-2-(2-pyridylthiomethyl)benzimidazole;
5-benzoyl-2-(2-pyridylthiomethyl)benzimidazole;
5-methoxy-2-(2-pyridylthiomethyl)benzimidazole;
2-[2-pyridylthio-(methyl)-methyl]benzimidazole;
5-benzoyl-2-(3,5-dimethyl-2-pyridylthiomethyl)benzimidazole;
5-benzoyl-2-(3-methyl-2-pyridylthiomethyl)benzimidazole;
2-(3-methyl-2-pyridylthiomethyl)benzimidazole;
2-(4-methyl-2-pyridylthiomethyl)benzimidazole;
5-trifluoromethyl-2-(4-methyl-2-pyridylthiomethyl)-benzimidazole;
5-carboxymethyl-2-(4-methyl-2-pyridylthiomethyl)benzimidazole;
5-carboxymethyl-2-(2-pyridylthiomethyl)benzimidazole;
5-benzoyl-2-(4-methyl-2-pyridylthiomethyl)benzimidazole;
5-methoxy-2-(4-methyl-2-pyridylthiomethyl)-bezimidazole;
5-acetyl-2-(4-methyl-2-pyridylthiomethyl)benzimidazole;
5-methyl-2-(4-methyl-2-pyridylthiomethyl)benzimidazole;
5,6-dimethyl-2-(4-methyl-2-pyridylthiomethyl)benzimidazole;
5-chloro-2-(4-methyl-2-pyridylthiomethyl)benzimidazole;
5-benzoyl-2-(2-pyridylsulfinylmethyl)benzimidazole;
2-(2-pyridylsulfinylmethyl)benzimidazole;
2-(5-nitro-2-pyridylsulfinylmethyl)benzimidazole;
5-methyl-2-(pyridylsulfinylmethyl)benzimidazole;
5,6-dimethyl-2-(2-pyridylsulfinylmethyl)benzimidazole;
5-chloro-2-(2-pyridylsulfinylmethyl)benzimidazole;
2-(2-benzimidazolylmethylsulfinyl)-4,6-dimethylpyrimidine;
5-trifluoromethyl-2-(2-pyridylsulfinylmethyl)benzimidazole;
5-methoxy-2-(2-pyridylsulfinylmethyl)benzimidazole;
erythro-2-[2-pyridylsulfinyl(methyl)methyl]benzimidazole;
threo-2-[2-pyridylsulfinyl(methyl)methyl]benzimidazole;
2-(1-oxido-2-pyridylsulfinylmethyl)benzimidazole;
2-(2-benzimidazolylmethylsulfinyl)pyrimidine;
5-benzoyl-2-(3,5-dimethyl-2-pyridylsulfinylmethyl)benzimidazole;
5-benzoyl-2-(3-methyl-2-pyridylsulfinylmethyl)benzimidazole;
2-(3-methyl-2-pyridylsulfinylmethyl)benzimidazole;
5-benzoyl-2-(4-methyl-2-pyridylsulfinylmethyl)benzimidazole;
5-carboxymethyl-2-(2-pyridylsulfinylmethyl)benzimidazole;
2-(4-methyl-2-pyridylsulfinylmethyl)benzimidazole;
5-trifluoromethyl-2-(4-methyl-2-pyridylsulfinylmethyl)benzimidazole;
5-carboxymethyl-2-(4-methyl-2-pyridylsulfinylmethyl)-benzimidazole;
5-methoxy-2-(4-methyl-2-pyridylsulfinylmethyl)benzimidazole;
5-acetyl-2-(4-methyl-2-pyridylsulfinylmethyl)benzimidazole;
5-methyl-2-(4-methyl-2-pyridylsulfinylmethyl)benzimidazole;
5,6-dimethyl-2-(4-methyl-2-pyridylsulfinylmethyl)benzimidazole;
5-chloro-2-(4-methyl-2-pyridylsulfinylmethyl)benzimidazole;
5-chloro-2-(2-pyridylsulfonylmethyl)benzimidazole;
2-(2-pyridylsulfonylmethyl)benzimidazole;
5-methyl-2-(2-pyridylsulfonylmethyl)benzimidazole;
5,6-dimethyl-2-(2-pyridylsulfonylmethyl)benzimidazole;
2-[2-pyridylsulfonyl(methyl)methyl]benzimidazole;
5-nitro-2-(2-pyridylsulfinylmethyl)benzimidazole;
5-benzoyl-1-methyl-2-(2-pyridylsulfinylmethyl)benzimidazole;
6-benzoyl-1-methyl-2-(2-pyridylsulfinylmethyl)benzimidazole;
5-benzoyl-1-carboxyethyl-2-(2-pyridylsulfinylmethyl)-benzimidazole;
6-benzoyl-1-carboxyethyl-2-(2-pyridylsulfinylmethyl)-benzimidazole;
1-ethyl-2-(2-pyridylsulfinylmethyl)benzimidazole; and pharmaceutically acceptable salts thereof.

3. A method for treating gastrointestinal diseases and inhibiting gastric acid secretion in an individual comprising the administration of the derivatives of formula I and their therapeutically acceptable salts according to claim 1 to an individual in need of said treatment in an amount effective to inhibit gastric acid secretion.

4. A pharmaceutical composition comprising at least one of the compounds of claim 1 in a pharmaceutically acceptable carrier.

5. The use of the derivatives of formula I and their physiologically acceptable salts as claimed in claim 1, for the manufacture of medicinal products intended for the treatment of gastrointestinal diseases, especially for the manufacture of agents which inhibit gastric acid secretion and of cytoprotective agents.

6. A method of cytoprotection comprising the administration of the compounds of at least one of claim 1 to an individual in need of said treatment in an amount effective to protect cells.

* * * * *

UNITED STATES PATENT OFFICE
CERTIFICATE OF CORRECTION

Patent No. 4,791,114                     Dated December 13, 1988

Inventor(s) Constansa et al.

It is certified that error appears in the above-identified patent and that said Letters Patent is hereby corrected as shown below:

Column 1, line 51, "atoms" should read --atom--.

Column 10, Table 3, last line, "713-5" should read --173-5--.

Column 15, line 52, "(d,1H)" should read --(d,1H);--.

Column 16, line 3, "trail" should read --trial--.

Column 16, line 12, "trail" should read --trial--.

Column 17, line 14, "H" should read --J--.

Signed and Sealed this

Eighteenth Day of July, 1989

Attest:

DONALD J. QUIGG

Attesting Officer          Commissioner of Patents and Trademarks